United States Patent
Takagi

(10) Patent No.: US 11,653,898 B2
(45) Date of Patent: May 23, 2023

(54) ULTRASOUND DIAGNOSTIC APPARATUS, ULTRASOUND IMAGE DISPLAY METHOD AND COMPUTER-READABLE RECORDING MEDIUM

(71) Applicant: Konica Minolta, Inc., Tokyo (JP)

(72) Inventor: Kazuya Takagi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 162 days.

(21) Appl. No.: 16/570,837

(22) Filed: Sep. 13, 2019

(65) Prior Publication Data

US 2020/0107819 A1 Apr. 9, 2020

(30) Foreign Application Priority Data

Oct. 5, 2018 (JP) .............................. JP2018-190444

(51) Int. Cl.
*A61B 8/08* (2006.01)
*A61B 8/00* (2006.01)
*A61B 8/14* (2006.01)

(52) U.S. Cl.
CPC .......... *A61B 8/5207* (2013.01); *A61B 8/0841* (2013.01); *A61B 8/14* (2013.01);
(Continued)

(58) Field of Classification Search
CPC ......... A61B 8/5207; A61B 8/463; A61B 8/14; A61B 8/5223; A61B 8/5246; A61B 8/0841

See application file for complete search history.

(56) References Cited

U.S. PATENT DOCUMENTS

2006/0293598 A1* 12/2006 Fraser .................... A61B 8/463
600/439
2009/0030322 A1* 1/2009 Fujiwara ............. G01S 7/52074
600/458

(Continued)

FOREIGN PATENT DOCUMENTS

JP 2000229098 A 8/2000
JP 2010187731 A 9/2010

(Continued)

OTHER PUBLICATIONS

Office Action dated Jul. 5, 2022 for the corresponding Japanese patent application No. 2018-190444, with English translation.

*Primary Examiner* — Keith M Raymond
*Assistant Examiner* — Andrew W Begeman
(74) *Attorney, Agent, or Firm* — Lucas & Mercanti, LLP

(57) ABSTRACT

An ultrasound diagnostic apparatus generates and displays an ultrasound image corresponding to reflected ultrasound reflected inside a subject. The ultrasound diagnostic apparatus includes a hardware processor that generates a B-mode image based on a reception signal corresponding to the reflected ultrasound, analyzes the B-mode image and determines an operation status of a treatment instrument used for treatment, and based on a result of the determination, displays a first display image including a current B-mode image and a second display image including a B-mode image obtained when the treatment instrument is in a non-operating state in such a manner that the first display image and second display image are aligned.

13 Claims, 7 Drawing Sheets

(52) U.S. Cl.
CPC ............ *A61B 8/463* (2013.01); *A61B 8/5223* (2013.01); *A61B 8/5246* (2013.01)

(56) References Cited

U.S. PATENT DOCUMENTS

| | | | | |
|---|---|---|---|---|
| 2009/0149754 | A1* | 6/2009 | Tsuda ........................ | A61B 8/14 600/439 |
| 2013/0137980 | A1* | 5/2013 | Waters ................ | A61B 18/1492 600/439 |
| 2015/0297172 | A1* | 10/2015 | Takagi ................. | G06K 9/4661 600/443 |
| 2017/0143295 | A1* | 5/2017 | Park ...................... | A61B 8/5207 |
| 2018/0168546 | A1* | 6/2018 | Ebata .................... | A61B 8/5215 |
| 2019/0380676 | A1* | 12/2019 | Swan ..................... | A61B 8/463 |

FOREIGN PATENT DOCUMENTS

| | | |
|---|---|---|
| JP | 2013220132 A | 10/2013 |
| JP | 2017080040 A | 5/2017 |

\* cited by examiner

ULTRASOUND DIAGNOSTIC APPARATUS, ULTRASOUND IMAGE DISPLAY METHOD AND COMPUTER-READABLE RECORDING MEDIUM

CROSS REFERENCE TO RELATED APPLICATIONS

The entire disclosure of Japanese Patent Application No. 2018-190444 filed on Oct. 5, 2018 is incorporated herein by reference in its entirety.

BACKGROUND

Technological Field

The present invention relates to an ultrasound diagnostic apparatus, an ultrasound image display method and a program and specifically relates to a technique that is useful when a treatment instrument is inserted into the body of a subject under ultrasound guidance and treatment is performed.

Description of Related Art

Conventionally, as one of medical image diagnostic apparatuses, an ultrasound diagnostic apparatus that transmits ultrasound toward a subject, receives waves reflected by the subject and performs predetermined signal processing on the reception signal to visualize a shape, a condition or behavior of the inside of the subject in the form of an ultrasound image is known. An ultrasound diagnostic apparatus can obtain an ultrasound image with a simple operation of applying an ultrasound probe to a body surface or inserting the ultrasound probe into the body and thus is safe and puts a smaller burden on the subject.

For example, an ultrasound diagnostic apparatus is used for treatment by inserting a treatment instrument into the body of a subject under ultrasound guidance to, for example, suck soft tissue in a treatment region of interest. In such treatment, a surgeon such as a doctor can insert the treatment instrument and perform treatment while viewing an ultrasound image obtained by the ultrasound diagnostic apparatus to confirm the treatment region of interest.

Where treatment is performed under ultrasound guidance, in order to grasp a correct position and range of a treatment region of interest, it is preferable that the treatment region of interest be clearly reflected in an ultrasound image (B-mode image). However, injection of fluid (for example, saline) from a treatment instrument inserted inside the body or ultrasound irradiation may cause generation of noise (hereinafter referred to as "spray pattern") in the ultrasound image, resulting in a decrease in visibility of the treatment region of interest.

In an ultrasound treatment apparatus disclosed in Japanese Patent Application Laid-Open No. 2000-229098, when treatment is performed using a treatment instrument, a live image during the treatment and a still image picked up, for example, before the treatment are displayed to ensure visibility of a treatment region of interest.

However, in the ultrasound diagnostic apparatus disclosed in Japanese Patent Application Laid-Open No. 2000-229098, a still image, for example, one before treatment, is displayed in response to an input of a driving start signal from a treatment instrument and the ultrasound diagnostic apparatus needs to include an interface for signal transmission/reception to/from the treatment instrument.

Also, a still image picked up, for example, before treatment is displayed as it is and thus identification of a treatment region of interest may be difficult depending on the level of skills of the surgeon.

SUMMARY

An object of the present invention is to provide an ultrasound diagnostic apparatus, an ultrasound image display method and a program that enable ensuring visibility of a treatment region of interest with no need for a special interface for connection with a treatment instrument.

Another object of the present invention is to provide an ultrasound diagnostic apparatus that enables identifying a treatment region of interest easily irrespective of a level of skills of a surgeon.

To achieve at least one of the abovementioned objects, according to an aspect of the present invention, an ultrasound diagnostic apparatus reflecting one aspect of the present invention is an apparatus for generating and displaying an ultrasound image corresponding to reflected ultrasound reflected inside a subject, the apparatus comprising a hardware processor that generates a B-mode image based on a reception signal corresponding to the reflected ultrasound, analyzes the B-mode image and determines an operation status of a treatment instrument used for treatment, displays, based on a result of the determination, a first display image including a current B-mode image and a second display image including a B-mode image obtained when the treatment instrument is in a non-operating state in such a manner that the first display image and the second display image are aligned.

To achieve at least one of the abovementioned objects, according to an aspect of the present invention, an ultrasound image display method reflecting one aspect of the present invention is a method for generating and displaying an ultrasound image corresponding to reflected ultrasound reflected inside a subject, the method comprising:
generating a B-mode image based on a reception signal corresponding to the reflected ultrasound;

analyzing the B-mode image and determining an operation status of a treatment instrument used for treatment; and displaying, based on a result of the determination, a first display image including a current B-mode image and a second display image including a B-mode image obtained when the treatment instrument is in a non-operating state in such a manner that the first display image and the second display image are aligned.

To achieve at least one of the abovementioned objects, according to an aspect of the present invention, a non-transitory computer-readable recording medium reflecting one aspect of the present invention is a medium storing a program for causing a computer in an ultrasound diagnostic apparatus for generating and displaying an ultrasound image corresponding to reflected ultrasound reflected inside a subject, to perform:

first processing for generating a B-mode image based on a reception signal corresponding to the reflected ultrasound;

second processing for analyzing the B-mode image and determining an operation status of a treatment instrument used for treatment; and third processing for displaying, based on a result of the determination by the second processing, a first display image including a current B-mode image and a second display image including a B-mode image obtained when the treatment instrument is in a non-operating state in such a manner that the first display image and the second display image are aligned.

To achieve at least one of the abovementioned objects, according to an aspect of the present invention, an ultrasound diagnostic apparatus reflecting one aspect of the present invention is an apparatus for generating and displaying an ultrasound image corresponding to reflected ultrasound reflected inside a subject, the apparatus comprising a hardware processor that generates a B-mode image based on a reception signal corresponding to the reflected ultrasound, determines an operation status of a treatment instrument used for treatment, displays, based on a result of the determination, a first display image including a current B-mode image and a second display image including a B-mode image obtained when the treatment instrument is in a non-operating state in such a manner that the first display image and the second display image are aligned, and highlights a treatment region of interest in the second display image.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

An embodiment of the present invention will be described in detail below with reference to the accompanying drawings.

Figure 1:
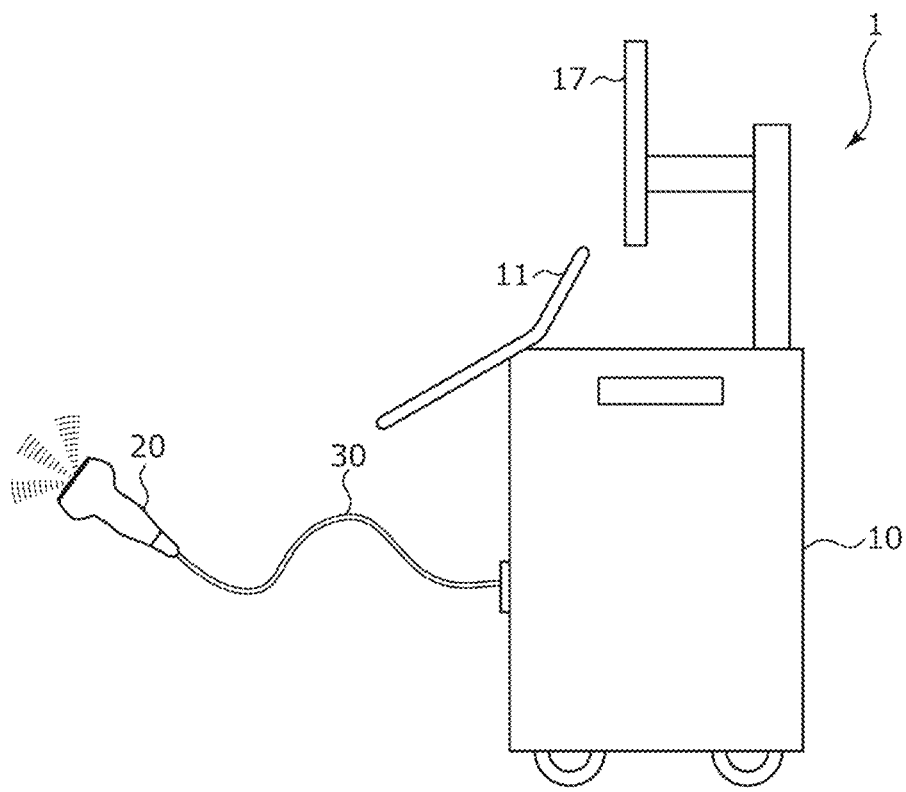
FIG. 1 is a diagram illustrating an outer appearance of an ultrasound diagnostic apparatus according to an embodiment.
Figure 2:
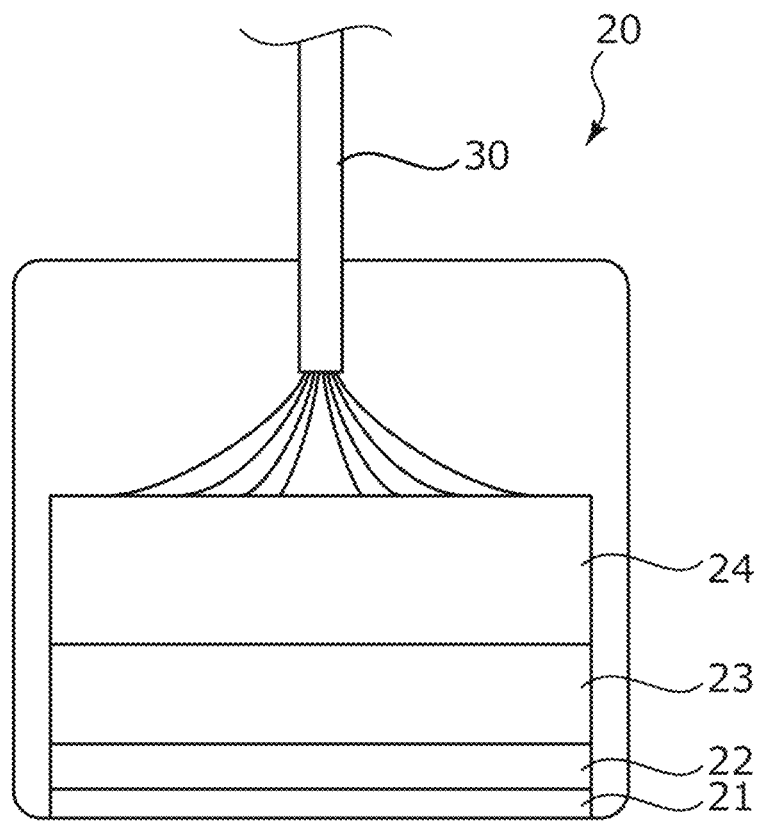
FIG. 2 is a diagram illustrating a configuration of an ultrasound probe.
Figure 3:
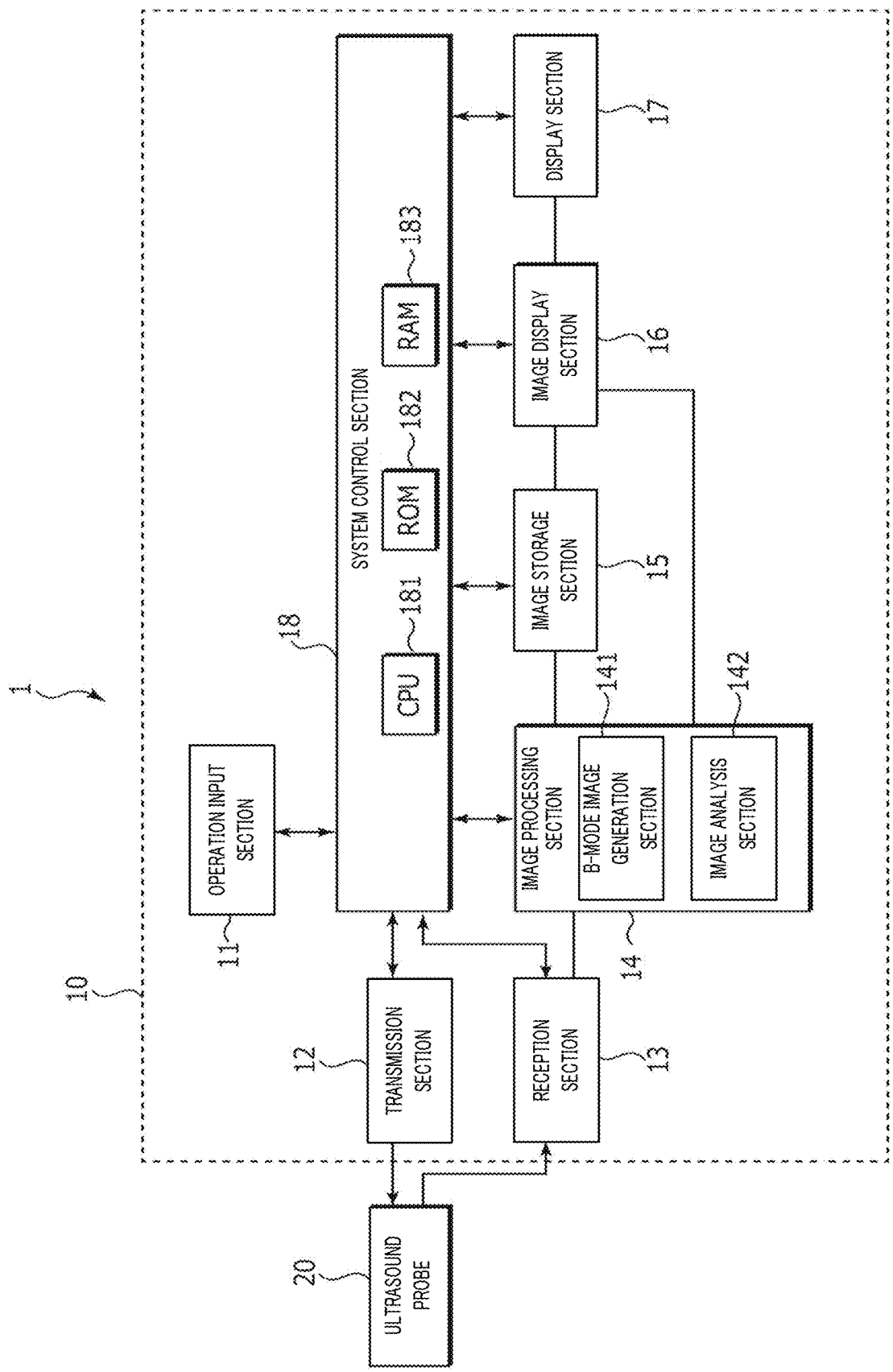
FIG. 3 is a block diagram illustrating a major part of a control system in the ultrasound diagnostic apparatus.

FIG. 1 is a diagram illustrating an outer appearance of ultrasound diagnostic apparatus 1 according to an embodiment of the present invention. FIG. 2 is a diagram illustrating a configuration of ultrasound probe 20. FIG. 3 is a diagram illustrating a major part of a control system in ultrasound diagnostic apparatus 1.

Ultrasound diagnostic apparatus 1 is used together with a treatment instrument and visualizes a state of the inside of a subject in the form of an ultrasound image to support treatment using the treatment instrument. When treatment is performed using a treatment instrument, a treatment mode is selected in ultrasound diagnostic apparatus 1.

Examples of the treatment instrument include one that creates a pressure-reduced portion at a distal end of a puncture part using the Venturi effect and sucks soft tissue of a treatment region of interest from the pressure-reduced portion to perform treatment (for example, TenJet (product name) manufactured by HydroCision, Inc.). The treatment instrument is equipped with a driving operation section, for example, a foot pedal, and can be activated/deactivated by operating the driving operation section.

Figure 4A:
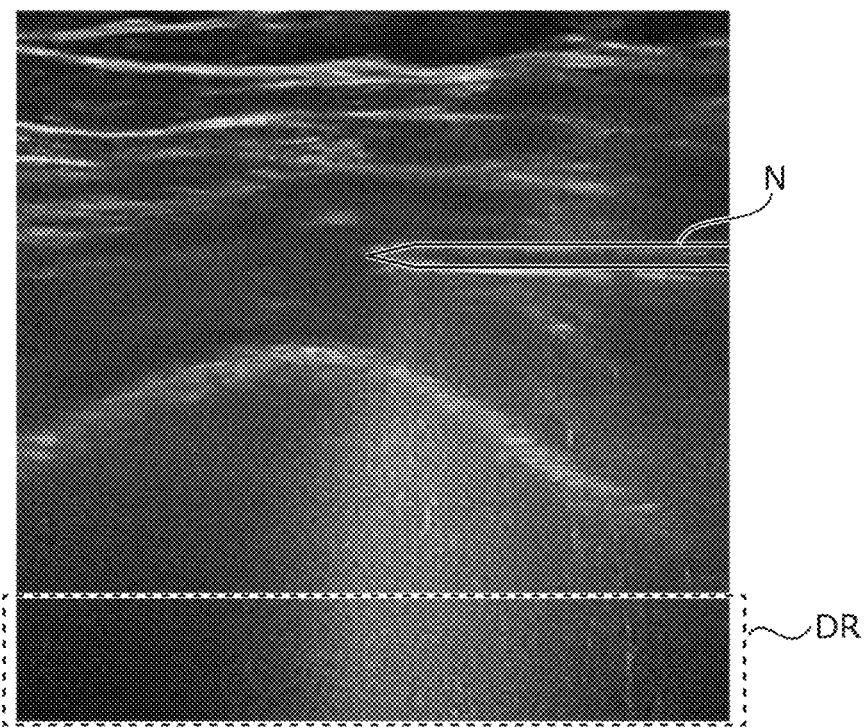
FIGS. 4A and 4B are diagrams illustrating an example of a B-mode image when a treatment instrument is in a non-operating state and an example of a B-mode image when the treatment instrument is in an operating state, respectively.
Figure 4B:
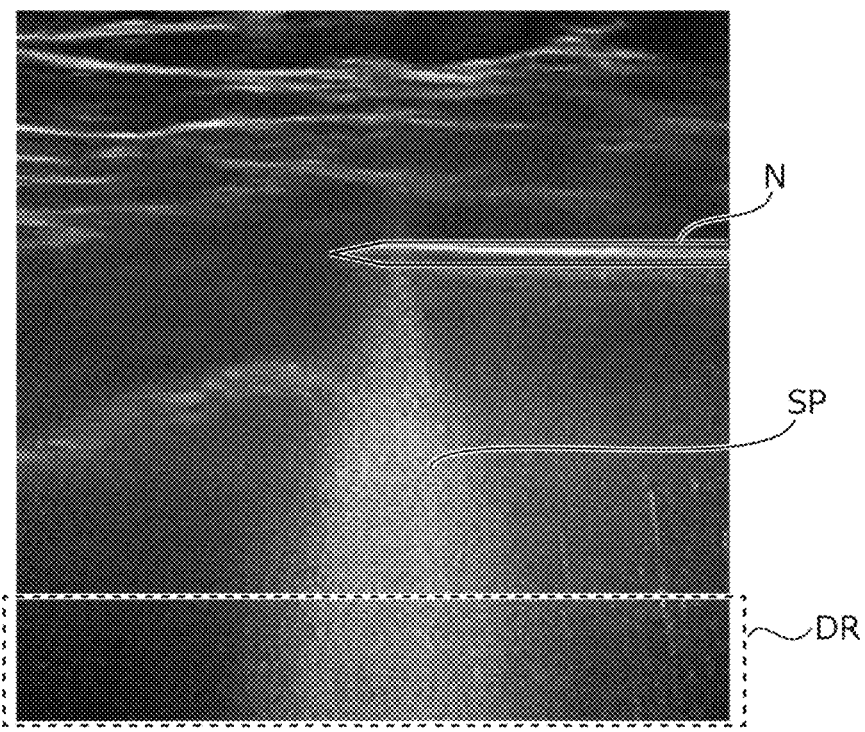

FIG. 4A is a diagram illustrating an example of an ultrasound image obtained in a non-operating state in which a treatment instrument is not activated and FIG. 4B is a diagram illustrating an example of an ultrasound image obtained in an operating state in which the treatment instrument is activated. Note that in each of FIGS. 4A and 4B, for ease of recognition of the inserted treatment instrument, puncture part N of the treatment instrument is illustrated with a line drawing superimposed thereon. The same applies to FIGS. 7A and 7B referred to later.

In the above-described treatment instrument, a significant amount of fluid is ejected from a suction port provided in the pressure-reduced portion, high-brightness spray pattern SP spreading downward from a distal end of puncture part N of the treatment instrument is shown in the ultrasound image (see FIG. 4B).

When the treatment instrument is inserted toward a treatment region of interest to perform treatment under ultrasound guidance, ultrasound diagnostic apparatus 1 displays a live image during the treatment as a first display image and a still image during a non-treatment period as a second display image, in response to a change in operation status (for example, activation/deactivation) of the treatment instrument. Since no spray pattern SP is shown in the second display image, visibility of the treatment region of interest is ensured.

Note that ultrasound diagnostic apparatus 1 has no need to include an interface for transmission/reception of a driving signal to/from treatment instrument, but may include such interface.

As illustrated in FIG. 1, ultrasound diagnostic apparatus 1 includes ultrasound diagnostic apparatus body 10 and ultrasound probe 20. Ultrasound diagnostic apparatus body 10 and ultrasound probe 20 are connected via cable 30. Note that ultrasound probe 20 may be connected to ultrasound diagnostic apparatus body 10 via wireless communication.

Ultrasound probe 20 transmits ultrasound to a subject, receives an ultrasound echo resulting from reflection of the ultrasound by the subject, converts the ultrasound echo into a reception signal and transmits the reception signal to ultrasound diagnostic apparatus body 10. For ultrasound probe 20, any electronic scanning probe such as a convex probe, a linear probe or a sector probe or a mechanical scanning probe such as a mechanical sector probe can be employed. The ultrasound probe 20 may include a puncture needle guide portion to which a puncture needle is attached, the puncture needle guide portion guiding a direction of puncture.

As illustrated in FIG. 2, ultrasound probe 20 includes acoustic lens 21, acoustic matching layer 22, transducer array 23 and backing material 24 in the order mentioned from the ultrasound transmission/reception side. Note that a protective layer may be disposed on a surface of acoustic lens 21 (ultrasound transmission/reception surface).

Acoustic lens 21 is a lens that converges ultrasound in a slice direction (direction orthogonal to a scanning direction in which a plurality of transducers are aligned), and for example, when a material, a sound propagation speed of which is lower than that of a living body, is used for the acoustic lens, generally has a semicylindrical shape in which a central portion in the slice direction thereof bulges.

Acoustic matching layer 22 is an intermediate substance for making ultrasound efficiently enter the subject and matches an acoustic impedance of the transducers (not illustrated) and an acoustic impedance of the subject with each other.

Transducer array 23 is formed of, for example, a plurality of strip transducers arranged in a single row in the scanning direction. In other words, ultrasound probe 20 is what is called a single-row probe.

Backing material 24 attenuates unwanted vibration caused by transducer array 23.

Ultrasound diagnostic apparatus body 10 visualizes a shape, a condition or behavior of the inside of the subject in the form of an ultrasound image (B-mode image), using the reception signal from ultrasound probe 20.

As illustrated in FIG. 3, ultrasound diagnostic apparatus body 10 includes, for example, operation input section 11, transmission section 12, reception section 13, image processing section 14, image storage section 15, image display section 16, display section 17 and system control section 18.

Each of transmission section 12, reception section 13, image processing section 14, image storage section 15 and image display section 16 is formed of, for example, a dedicated or general-purpose hardware (electronic circuit) for relevant processing, such as a DSP (digital signal processor), an ASIC (application-specific integrated circuit) or a PLD (programmable logic device), and provides a relevant function in cooperation with system control section 18.

Operation input section 11 receives an input of, for example, a command for providing an instruction to, for example, start an examination or information relating to the subject. Operation input section 11 is formed of, for example, an operation panel including a plurality of input switches, a keyboard and a mouse. Note that operation input section 11 may be formed of a touch panel integrated with display section 17.

Transmission section 12 generates a transmission signal (driving signal) and outputs the transmission signal to ultrasound probe 20 according to an instruction from system control section 18. Although not illustrated, transmission section 12 includes, for example, a clock generation circuit, a pulse generation circuit, a pulse width setting section and a delay circuit.

The clock generation circuit generates a clock signal based on which a pulse signal transmission timing and a transmission frequency are determined. The pulse generation circuit generates a bipolar rectangular-wave pulse having a preset voltage amplitude in a predetermined cycle. The pulse width setting section sets a pulse width of rectangular-wave pulses to be output from the pulse generation circuit. The rectangular-wave pulses generated in the pulse generation circuit are separated into different wirings for the respective transducers of ultrasound probe 20 before or after being input to the pulse width setting section. The delay circuit delays the generated rectangular-wave pulses according to transmission timings for the respective transducers and outputs the generated rectangular-wave pulses to the respective transducers.

Reception section 13 receives the reception signal from ultrasound probe 20 and outputs the reception signal to image processing section 14 according to an instruction from system control section 18. Although not illustrated, reception section 13 includes, for example, an amplifier, an A/D conversion circuit and a phase-adjustment/addition circuit.

The amplifier amplifies reception signals corresponding to ultrasounds received by the respective transducers of ultrasound probe 20 at a predetermined amplification ratio set in advance. The A/D conversion circuit converts the amplified reception signals into digital data at a predetermined sampling frequency. The phase-adjustment/addition circuit provides delays to the respective reception signals resulting from the A/D conversion for the respective wirings for the transducers to adjust time phases of the reception signals and adds up the reception signals (phase-adjustment and addition).

Image processing section 14 includes B-mode image generation section 141 and image analysis section 142. Also, although not illustrated, image processing section 14 includes a DSC (digital scan converter) that performs coordinate conversion and pixel interpolation according to the type of ultrasound probe 20.

B-mode image generation section 141 generates a B-mode image indicating a state of the inside of the subject based on the reception signal, in accordance with an instruction from system control section 18. When the treatment instrument is inserted inside the subject, puncture part N of the treatment instrument is shown in the B-mode image (see FIGS. 4A and 4B). Also, spray pattern SP spreading from the distal end of puncture part N toward a deep part is shown in a B-mode image during treatment in which the treatment instrument is active (see FIG. 4B).

Image analysis section 142 analyzes a B-mode image and determines a change in operation status of the treatment instrument. For example, image analysis section 142 determines whether the treatment instrument is in an on-state (during treatment) or in an off-state (during a non-treatment period). A method for determination of a change in state of the treatment instrument will be described later.

Image storage section 15 is formed of, for example, a non-volatile semiconductor memory (what is called a flash memory) or a hard disk drive. Image storage section 15 may be a disk drive that drives an optical disk such as a CD (compact disc), a DVD (digital versatile disc) or a BD (Blu-ray disc ("Blu-ray" is a registered trademark)) or a magneto-optical disk such as an MO (magneto-optical disc) to read/write information.

Image storage section 15 stores image data generated in B-mode image generation section 141 on a frame-by-frame basis. The image data stored in the image storage section 15 is read out according to an instruction from system control section 18 and used for analysis by image analysis section 142 or used for display on display section 17.

Image display section 16 converts data of a B-mode image generated in image processing section 14 (which may be data stored in image storage section 15) into a display signal that is compatible with display section 17 and outputs the display signal according to an instruction from system control section 18. In the present embodiment, when ultrasound diagnostic apparatus 1 is used together with a treatment instrument, image display section 16 provides two-screen display in which two B-mode images are aligned (see FIGS. 7A and 7B). In the two-screen display, first display image D1 is a current B-mode image and second display image D2 is a B-mode image obtained when the treatment instrument is in a non-operating state.

Display section 17 is formed of, for example, a liquid-crystal display, an organic EL display or a CRT display. Display section 17 displays a display image based on a display signal from image display section 16, in accordance with an instruction from system control section 18.

System control section 18 performs overall control of ultrasound diagnostic apparatus 1 by controlling operation input section 11, transmission section 12, reception section 13, image processing section 14, image storage section 15, image display section 16 and display section 17 according to the respective functions.

System control section 18 includes, for example, CPU (central processing unit) 181, which serves as an arithmetic/control device, and ROM (read-only memory) 182 and RAM (random access memory) 183, which serve as a main memory device. A basic program and basic setting data are stored in ROM 182. Also, a treatment support program to be executed in the treatment mode is stored in ROM 182. CPU 181 performs centralized control of operation of the respective functional blocks (transmission section 12, reception section 13, image processing section 14, image storage section 15, image display section 16 and display section 17) of ultrasound diagnostic apparatus body 10, by reading a program according to the content of processing from ROM 182, loading the program to RAM 183 and executing the loaded program.

In the present embodiment, the functions of the respective functional blocks are fulfilled by cooperation between the respective pieces of hardware forming the functional blocks and system control section 18. Note that some or all of the functions of the respective functional blocks may be fulfilled by execution of programs by system control section 18.

Figure 5:
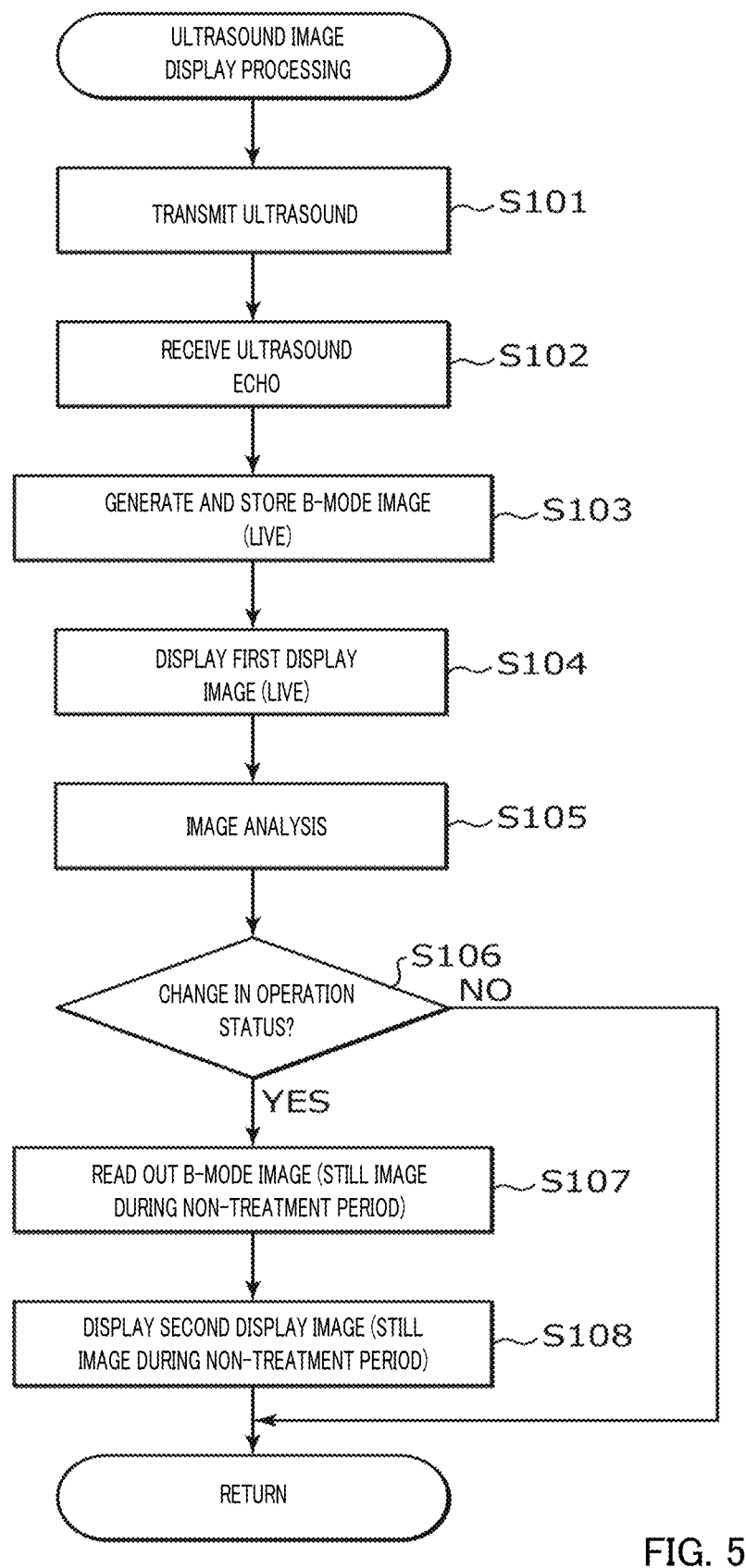
FIG. 5 is a diagram illustrating an example of ultrasound image display processing.

FIG. 5 is a flowchart illustrating an example of ultrasound image display processing where ultrasound diagnostic apparatus 1 is used together with a treatment instrument. This processing is fulfilled, for example, by execution of a predetermined program (treatment support program) stored in ROM 182 by CPU 181 in response to enabling of the treatment mode in ultrasound diagnostic apparatus 1. The enabling of the treatment mode is performed by, for example, mode selection via operation input section 11.

In step S101, system control section 18 controls transmission section 12 to transmit ultrasound from ultrasound probe 20.

In step S102, system control section 18 controls reception section 13 to acquire a reception signal corresponding to reflected ultrasound (ultrasound echo) received by ultrasound probe 20.

In step S103, system control section 18 controls image processing section 14 (B-mode image generation section 141) to generate a B-mode image based on the reception signal and store the B-mode image in image storage section 15.

In step S104, system control section 18 controls image display section 16 and display section 17 to display a current B-mode image (live image) as first display image D1. Note that second display image D2 is not specifically limited before a start of treatment using the treatment instrument (except resumption of treatment). For example, as second display image D2, a B-mode image before insertion of the treatment instrument may be displayed or the current B-mode image may be displayed.

Figure 6A:
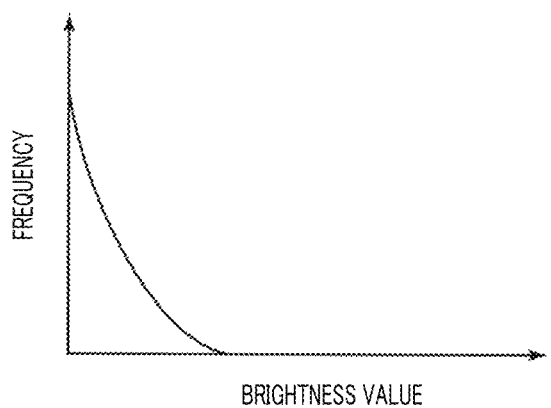
FIGS. 6A to 6C are diagrams for describing a method for determining an operation status of the treatment instrument based on a brightness distribution.

In step S105, system control section 18 controls image processing section 14 (image analysis section 142) to analyze a brightness distribution in the generated B-mode image. More specifically, system control section 18 generates a graph of brightness values in a predetermined region (see FIGS. 6A and 6B). FIG. 6A is a graph when the treatment instrument is in a non-operating state and FIG. 6B is a graph when the treatment instrument is in an operating state.

Here, it is preferable that the predetermined region that is subject to the analysis of the B-mode image be, for example, a deep region (region DR surrounded by the dotted line in each of FIGS. 4A and 4B) in the B-mode image. When the present function is used, a user sets a display depth in such a manner that a treatment region of interest is displayed in an upper part with reference to a center of the screen. Therefore, the deep region (for example, a lower region corresponding to 20% of the B-mode image) is displayed as a relatively-low brightness (black display) image. Then, upon high-brightness spray pattern SP being shown, a change occurs in brightness distribution. Therefore, detection of a change in brightness distribution of the deep region is favorable for determination of a change in operation status of the treatment instrument, more specifically, determines whether the treatment instrument is activated or deactivated. Note that an entirety of the B-mode image may be subject to analysis or a particular region other than the deep region may be subject to analysis.

Next, in step S106 in FIG. 5, system control section 18 controls image processing section 14 (image analysis section 142) to determine whether or not the operation status of the treatment instrument has changed, based on a result of the analysis.

Figure 6B:
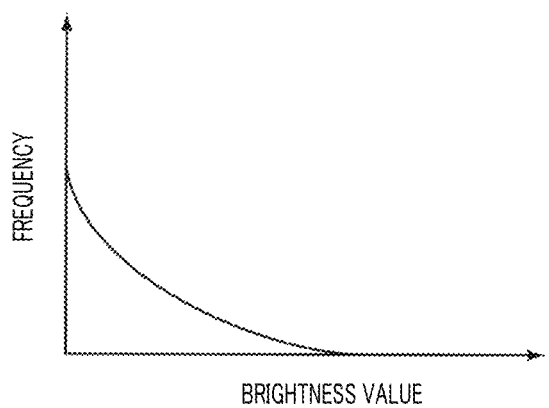

As illustrated in FIGS. 6A and 6B, in a case where the treatment instrument has been switched from a non-operating state to an operating state, high-brightness spray pattern SP is shown, causing an increase of high brightness-side frequencies. On the other hand, in a case where the treatment instrument has been switched from an operating state to a non-operating state, high-brightness spray pattern SP disappears, causing a decrease in high brightness-side frequencies. Therefore, comparison between a brightness distribution obtained last time and a brightness distribution obtained the present time enables determination of whether or not the operation status of the treatment instrument has changed.

Figure 6C:
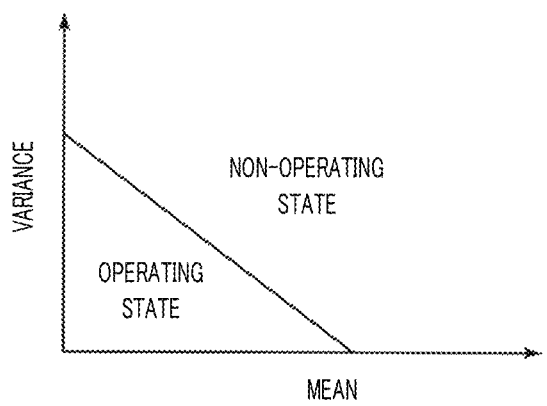

Also, in the graphs in FIGS. 6A and 6B, when the treatment instrument is in an operating state (see FIG. 6B), a mean and variance of brightness values are large in comparison with a case where the treatment instrument is in a non-operating state (see FIG. 6A). Therefore, whether or not the operation status of the treatment instrument has changed can be determined using a mean and variance of brightness values calculated from a brightness distribution. For example, as illustrated in FIG. 6C, whether the treatment instrument is in an operating state or in a non-operating state can be determined according to a linear discriminant using a set of a mean and variance of brightness values (means, variance). Also, for example, whether treatment instrument is in an operating state or in a non-operating state may be determined by comparing one of the mean and the variance of brightness values with a threshold value for the one.

In a case where the operation status of the treatment instrument has changed ("YES" in step S106), the processing proceeds to the processing in the step S107. In a case where the treatment instrument has been activated from an inactive state and treatment (suction) has been started or in a case where the treatment instrument has been deactivated from an active state and the treatment has been finished (which may be a temporary end), the processing in step S107 is performed. In a case where the operation status of the treatment instrument has not changed ("NO" in step S106), the processing proceeds to the processing in step S101. In this case, the treatment instrument is kept inactive or kept active, display of second display image D2 is maintained and only the live image displayed as first display image D1 is updated.

In step S107, system control section 18 controls image storage section 15 to read out a B-mode image obtained during a non-treatment period in which the treatment instrument is a non-operating state.

More specifically, in a case where the treatment instrument has been switched from a non-operating state to an operating state, a B-mode image before treatment is read out. In this case, the read-out B-mode image is preferably one immediately before the treatment instrument enters the operating state.

Also, in a case where the treatment instrument has been changed from an operating state to a non-operating state, a B-mode image after the treatment is read out. For example, in step S106, arrangement is made so as to, in a case where the status has been maintained for a certain period of time after the change in brightness distribution in the predetermined region, determine that the operation status of the treatment instrument has changed, enabling reading out a still image during a non-treatment period (after treatment) in which no spray pattern SP is shown.

In step S108, system control section 18 controls image display section 16 and display section 17 to display the read-out B-mode image (still image during a non-treatment period) as second display image D2. Then, the processing returns to step S101 and repeated until completion of the treatment.

Figure 7A:
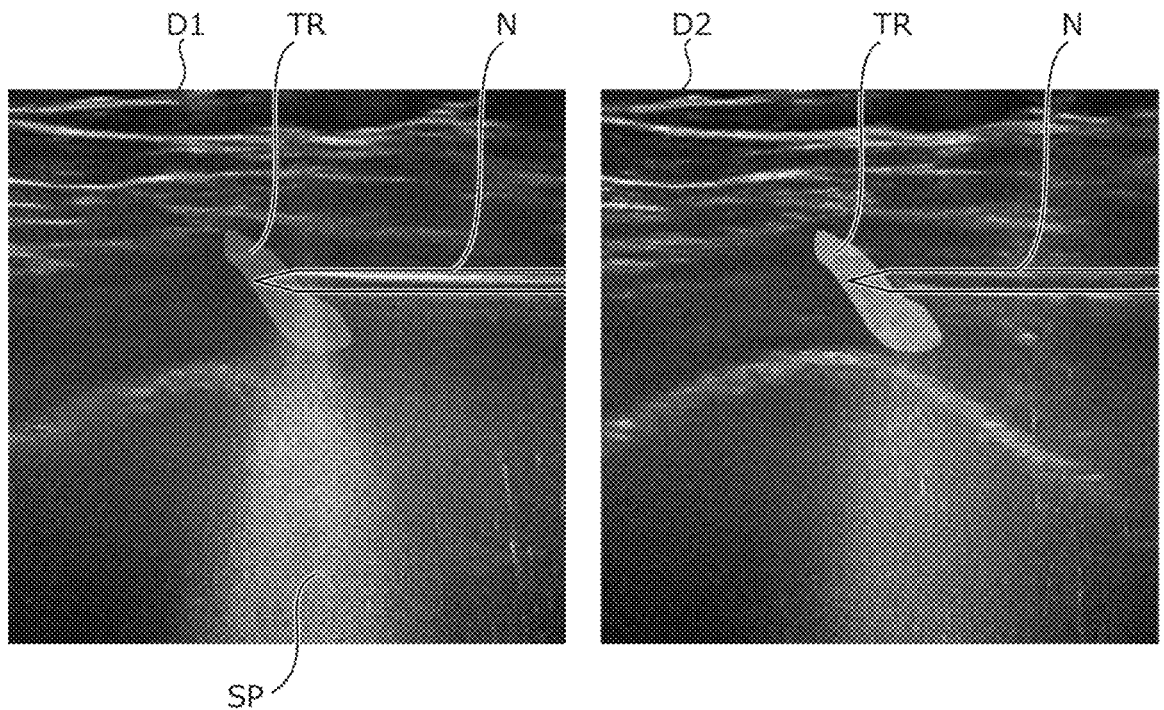
FIGS. 7A and 7B are diagrams illustrating example display images when the treatment instrument is in an operating state (during treatment) and example display images when the treatment instrument is in a non-operating state (after treatment).

In a case where the treatment instrument has been switched from a non-operating state to an operating state, display section 17 provides two-screen display of first display image D1 (live image) and second display image D2 (still image before the treatment) (see FIG. 7A). Since no spray pattern SP is shown in second display image D2, treatment region of interest TR can easily be identified. A surgeon can perform treatment while confirming treatment region of interest TR by comparing first display image D1 and second display image D2.

Figure 7B:
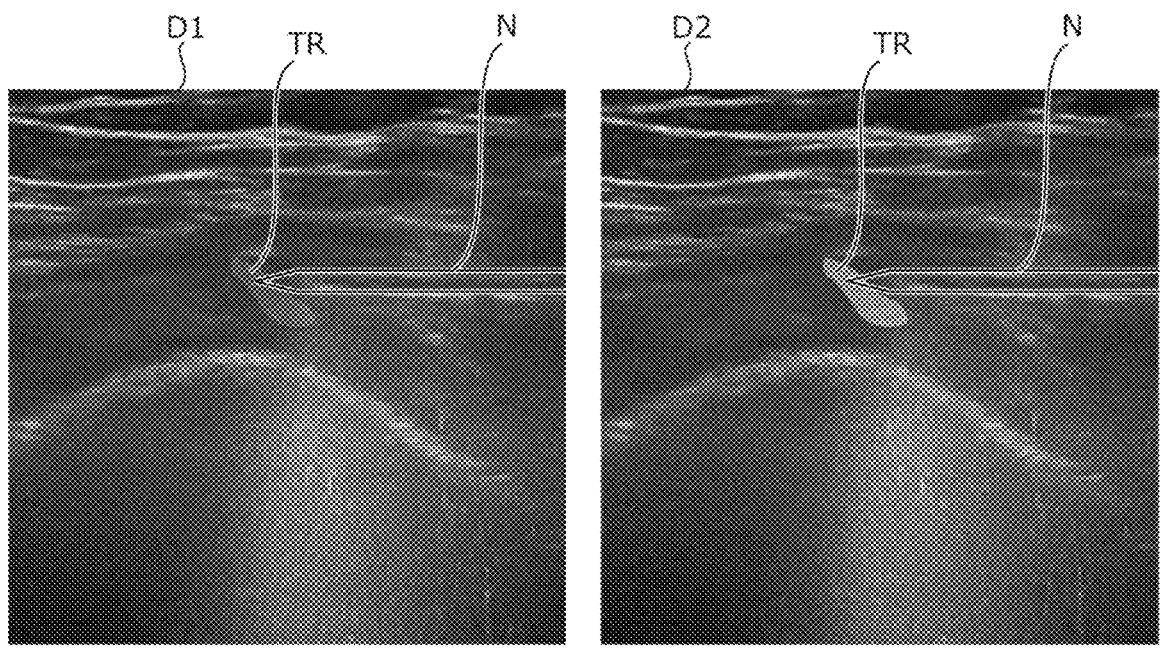

Also, in a case where the treatment instrument has been switched from an operating state to a non-operating state, display section 17 provides two-screen display of first display image D1 (live image) and second display image D2 (still image after the treatment) (see FIG. 7B). Since no spray pattern SP is shown in second display image D2, treatment region of interest TR can easily be identified. Also, since second display image D2 is a still image after treatment, the surgeon can confirm a status of progress of the treatment regarding to which extent the treatment region of interest remains, and thus can properly perform the treatment until the treatment region of interest is fully removed.

Note that in a case where the treatment instrument has been switched from an operating state to a non-operating state and then switched to an operating state, that is, in a case where treatment is resumed after an interruption, a still image immediately before the resumption of the treatment is displayed as second display image D2. Then, in a case where the treatment instrument has been switched from the operating state to a non-operating state, a new B-mode image (still image after an end of the resumed treatment) is read out by the processing in steps S107 and S108 and second display image D2 is thereby updated.

In the above-described ultrasound image display processing, it is preferable that when second display image D2 is displayed in step S108, the treatment region of interest is highlighted. Examples of the highlighting include coloring. As illustrated in FIGS. 7A and 7B, treatment region of interest TR in second display image D2 is shown more clearly than treatment region of interest TR in first display image D1.

Since a treatment region of interest is softer or more slurry than the surrounding bone and body tissue, the treatment region of interest is shown with a brightness that is lower than the surroundings. Therefore, it is possible to analyze a B-mode image, detect a tissue region, identify a low-brightness region in the tissue region as a treatment region of interest and highlight treatment region of interest TR.

In step S108, as a result of the treatment region of interest in second display image D2 being subjected to highlighting processing, the surgeon can confirm to which extent the treatment has been performed and whether or not the treatment has correctly been performed, by comparing the images before and after the treatment and thus can perform the treatment properly. In other words, the surgeon can easily identify a treatment region of interest irrespective of the level of his/her skills and thus can more properly perform the treatment.

As described above, ultrasound diagnostic apparatus 1 according to the embodiment is an ultrasound diagnostic apparatus for generating and displaying an ultrasound image corresponding to reflected ultrasound reflected inside a subject, the apparatus including: B-mode image generation section 141 that generates a B-mode image based on a reception signal corresponding to the reflected ultrasound; image analysis section 142 (determination section) that analyzes the B-mode image and determines an operation status of a treatment instrument used for treatment; and image display section 16 that based on a result of the determination by image analysis section 142, displays first display image D1 including a current B-mode image and second display image D2 including a B-mode image obtained when the treatment instrument is in a non-operating state in such a manner that first display image D1 and second display image D2 are aligned.

Also, the ultrasound image display method according to the embodiment is an ultrasound image display method for generating and displaying an ultrasound image corresponding to reflected ultrasound reflected inside a subject, the method including: a first step of generating a B-mode image based on a reception signal corresponding to the reflected ultrasound (step S103 in FIG. 5); a second step of analyzing the B-mode image and determining an operation status of a treatment instrument used for treatment (steps S105 and S106 in FIG. 5) and a third step of, based on a result of the determination in the second step, displaying first display image D1 including a current B-mode image and second display image D2 including a B-mode image obtained when the treatment instrument is in a non-operating state in such a manner that first display image D1 and second display image D2 are aligned (steps S107 and S108 in FIG. 5).

Also, the program according to the embodiment causes system control section 18 (computer) in ultrasound diagnostic apparatus 1 for generating and displaying an ultrasound image corresponding to reflected ultrasound reflected inside a subject, to perform: first processing for generating a B-mode image based on a reception signal corresponding to the reflected ultrasound (step S103 in FIG. 5); second processing for analyzing the B-mode image and determining an operation status of a treatment instrument used for treatment (steps S105 and S106 in FIG. 5); and third processing for, based on a result of the determination by the second processing, displaying first display image D1 including a current B-mode image and second display image D2 including a B-mode image obtained when the treatment instrument is in a non-operating state in such a manner that first display image D1 and second display image D2 are aligned (steps S107 and S108 in FIG. 5).

This program is provided via, for example, a computer-readable removable storage medium (which may be an optical disk, a magneto-optical disk or a memory card) with the program stored therein. Also, for example, this program can be provided by being downloaded via a network from a server that holds the program.

According to ultrasound diagnostic apparatus 1, the ultrasound image display method and the program according to the embodiment, even when visibility of treatment region of interest TR is lowered by spray pattern SP in first display image D1 including a live image, no spray pattern SP is shown in second display image D2 including a still image during a non-treatment period, the still image being obtained when the treatment instrument is in a non-operating state, and thus visibility of treatment region of interest TR is ensured. Therefore, a surgeon can properly perform treatment while confirming treatment region of interest TR in second display image D2.

Also, the operation status of the treatment instrument is determined by means of image analysis and thus there is no need to provide a special interface for connection with the treatment instrument in ultrasound diagnostic apparatus 1. Therefore, reduction in cost of ultrasound diagnostic apparatus 1 can be achieved.

Also, in ultrasound diagnostic apparatus 1, image analysis section 142 (determination section) determines whether the treatment instrument is activated or deactivated. Consequently, ultrasound diagnostic apparatus 1 can properly respond to a case where noise (for example, spray pattern SP) is shown in a B-mode image depending on the operation status of the treatment instrument.

Also, in ultrasound diagnostic apparatus 1, image analysis section 142 (determination section) determines a change in operation status of the treatment instrument. Consequently, proper second display image D2 can be displayed according to a case where the treatment instrument has been switched from a non-operating state to an operating state or a case where the treatment instrument has been switched from an operating state to a non-operating state.

Also, in ultrasound diagnostic apparatus 1, image analysis section 142 (determination section) determines the operation status of the treatment instrument based on a change in brightness distribution in a predetermined region in a B-mode image.

More specifically, image analysis section 142 (determination section) determines the operation status of the treatment instrument based on at least one of a mean and variance of brightness values in the predetermined region.

Consequently, the operation status of treatment instrument can be determined by relatively simple processing and thus a processing load on system control section 18 can be reduced.

Also, in ultrasound diagnostic apparatus 1, a predetermined region that is subject to image analysis is a deep region in the B-mode image. Consequently, a change in brightness distribution accompanying a change in operation status of the treatment instrument is conspicuously indicated, enabling easy and correct determination of the operation status of the treatment instrument.

Also, in ultrasound diagnostic apparatus 1, when the treatment instrument has been switched from a non-operating state to an operating state, image display section 16 displays second display image D2 including a B-mode image obtained immediately before the switching. Consequently, no spray pattern SP is shown in second display image D2 and thus treatment region of interest TR can easily be identified, enabling the surgeon to proceed treatment while confirming treatment region of interest TR by comparing first display image D1 and second display image D2 with each other.

Also, in ultrasound diagnostic apparatus 1, when the treatment instrument has been switched from an operating state to a non-operating state, image display section 16 displays second display image D2 including a B-mode image immediately after the switching. Since second display image D2 is a still image after treatment, the surgeon can confirm a status of progress of the treatment regarding to which extent the treatment region of interest remains and thus can properly perform the treatment until completion of removal of the treatment region of interest.

Also, in ultrasound diagnostic apparatus 1, image display section 16 highlights the treatment region of interest in the second display image. More specifically, the treatment region of interest has a brightness that is lower than that of a region around the treatment region of interest. Consequently, the surgeon can easily identify the treatment region of interest regardless of the level of his/her skills and can further properly perform the treatment.

Furthermore, the present embodiment also discloses an aspect of the invention as follows.

Ultrasound diagnostic apparatus 1 according to the embodiment is an ultrasound diagnostic apparatus for generating and displaying an ultrasound image corresponding to reflected ultrasound reflected inside a subject, the apparatus including: B-mode image generation section 141 that generates a B-mode image based on a reception signal corresponding to the reflected ultrasound; image analysis section 142 (determination section) that determines an operation status of a treatment instrument used for treatment; and image display section 16 that based on a result of the determination by image analysis section 142, displays first display image D1 including a current B-mode image and second display image D2 including a B-mode image obtained when the treatment instrument is in a non-operating state in such a manner that first display image D1 and second display image D2 are aligned Image display section 16 highlights treatment region of interest TR in second display image D2.

Consequently, a surgeon can easily identify a treatment region of interest irrespective of the level of his/her skills and thus can properly perform treatment.

Note that in this case, the determination section may be configured so as to determine the operation status of the treatment instrument based on a driving signal from the treatment instrument, rather than image analysis.

Although an invention made by the present inventor has been described above based on an embodiment, the present invention is not limited to the above embodiment and can be changed without departing from the spirit of the invention.

For example, image display section 16 may be configured so as to display information relating to the area of treatment region of interest TR. As the information relating to the area of treatment region of interest TR, for example, the area of a low-brightness region may be indicated by a numerical value in a screen (for example, a lower part of the screen) or may be indicated by a graph. Indication of the area of the low-brightness region before treatment and the area of the low-brightness region after treatment by respective numerical values or graphs enables visually confirming to which extend treatment has been performed. Also, for example, image display section 16 may be configured to indicate a degree of reduction of the area of the low-brightness region after treatment relative to the area of the low-brightness region before the treatment (for example, "−10" when the degree of reduction is 10). Consequently, a result of the treatment can easily be confirmed.

Also, a B-mode image obtained during a non-treatment period (before treatment), the B-mode image being read out when the treatment instrument has been switched from a non-operating state to an operating state, may be a B-mode image obtained several frames before the treatment instrument enters the operating state, rather than a B-mode image immediately before the treatment instrument enters the operating state. This is because in the case of the frame immediately before, a spray pattern may be shown slightly.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound diagnostic apparatus for generating and displaying an ultrasound image corresponding to a reflected ultrasound reflected inside a subject, the apparatus comprising a hardware processor that
   generates a current B-mode image based on a reception signal corresponding to the reflected ultrasound,
   analyzes the current B-mode image and determines an operation status of a treatment instrument used for treatment, the operation status being determined based on whether a spray pattern is present in the current B-mode image, and the spray pattern being determined based on a change in a brightness distribution in a low or bottom region in the current B-mode image,
   displays, in response to a determination that the spray pattern is present in the current B-mode image, a first display image including the current B-mode image and a second display image including a non-operating state B-mode image obtained when the treatment instrument is in a non-operating state in such a manner that the first display image and the second display image are aligned.

2. The ultrasound diagnostic apparatus according to claim 1, wherein the hardware processor determines whether the treatment instrument is activated or deactivated.

3. The ultrasound diagnostic apparatus according to claim 1, wherein the hardware processor determines a change in the operation status of the treatment instrument.

4. The ultrasound diagnostic apparatus according to claim 1, wherein the hardware processor determines the operation status of the treatment instrument based on at least one of an average and variance of brightness values in the low or bottom region in the current B-mode image.

5. The ultrasound diagnostic apparatus according to claim 1, wherein the hardware processor generates a live B-mode image and determines a change in operation status by analyzing the live B-mode image, and when the determination of the change in operation status is that the treatment instrument has been switched from the non-operating state to the operating state, the hardware processor displays the second display image including the non-operating state B-mode image obtained before the switching.

6. The ultrasound diagnostic apparatus according to claim 1, wherein the hardware processor generates a live B-mode image and determines a change in operation status by analyzing the live B-mode image, and when the determination of the change in operation status is that the treatment instrument has been switched from the operating state to the non-operating state, the hardware processor displays the second display image including the non-operating state B-mode image obtained after the switching.

7. The ultrasound diagnostic apparatus according to claim 1, wherein the hardware processor highlights a treatment region of interest in the second display image.

8. The ultrasound diagnostic apparatus according to claim 7, wherein the treatment region of interest is identified by the hardware processor as having a brightness that is lower than that of a region around the treatment region of interest.

9. The ultrasound diagnostic apparatus according to claim 1, wherein the low or bottom region is in a bottom 20% of the current B-mode image.

10. An ultrasound image display method for generating and displaying an ultrasound image corresponding to a reflected ultrasound reflected inside a subject, the method comprising:
    generating a current B-mode image based on a reception signal corresponding to the reflected ultrasound;
    analyzing the current B-mode image and determining an operation status of a treatment instrument used for treatment, the operation status being determined based on whether a spray pattern is present in the current B-mode image, and the spray pattern being determined based on a change in a brightness distribution in a low or bottom region in the current B-mode image; and
    displaying, in response to a determination that the spray pattern is present in the current B-mode image, a first display image including the current B-mode image and a second display image including a non-operating state B-mode image obtained when the treatment instrument is in a non-operating state in such a manner that the first display image and the second display image are aligned.

11. A non-transitory computer-readable recording medium storing a program for causing a computer in an ultrasound diagnostic apparatus for generating and displaying an ultrasound image corresponding to a reflected ultrasound reflected inside a subject, to perform:
    first processing for generating a current B-mode image based on a reception signal corresponding to the reflected ultrasound;
    second processing for analyzing the current B-mode image and determining an operation status of a treatment instrument used for treatment, the operation status being determined based on whether a spray pattern is present in the current B-mode image, and the spray pattern being determined based on a change in a brightness distribution in a low or bottom region in the current B-mode image; and
    third processing for displaying, in response to a determination that the spray pattern is present in the current B-mode image by the second processing, a first display image including the current B-mode image and a second display image including a non-operating state B-mode image obtained when the treatment instrument is in a non-operating state in such a manner that the first display image and the second display image are aligned.

12. An ultrasound diagnostic apparatus for generating and displaying an ultrasound image corresponding to a reflected ultrasound reflected inside a subject, the apparatus comprising a hardware processor that
- generates a current B-mode image based on a reception signal corresponding to the reflected ultrasound,
- determines an operation status of a treatment instrument used for treatment, the operation status being determined based on whether a spray pattern is present in the current B-mode image, and the spray pattern being determined based on a change in a brightness distribution in a low or bottom region in the current B-mode image,
- displays, in response to a determination that the spray pattern is present in the current B-mode image, a first display image including the current B-mode image and a second display image including a non-operating state B-mode image obtained when the treatment instrument is in a non-operating state in such a manner that the first display image and the second display image are aligned, and highlights a treatment region of interest in the second display image.

13. The ultrasound diagnostic apparatus according to claim 12, wherein the hardware processor displays information relating to an area of the treatment region of interest.

* * * * *